United States Patent [19]

Barabash et al.

[11] Patent Number: 5,797,845

[45] Date of Patent: Aug. 25, 1998

[54] ULTRASOUND APPARATUS FOR THREE DIMENSIONAL IMAGE RECONSTRUCTION

[76] Inventors: Leonid S. Barabash, 13021 S. 48th St., Apt. 2097; Aaron E. LaBarge, 3914 E. Nambe St., both of Phoenix, Ariz. 85044; Angel T. M. Wang, 4700 Sandyland Rd. Apt. 37, Carpenteria, Calif. 93013

[21] Appl. No.: 742,403

[22] Filed: Nov. 4, 1996

[51] Int. Cl.$^6$ .................................................. A61B 8/00
[52] U.S. Cl. ........................ 600/443; 600/459; 128/916
[58] Field of Search .................. 128/916, 660.07, 128/660.01, 661.01; 600/443, 447, 459

[56] References Cited

U.S. PATENT DOCUMENTS

| | | |
|---|---|---|
| 4,766,554 | 8/1988 | Sarr et al. |
| 4,949,310 | 8/1990 | Smith et al. ................... 128/660.01 |
| 5,103,129 | 4/1992 | Slayton et al. |
| 5,159,931 | 11/1992 | Pini . |

OTHER PUBLICATIONS

Chris M.W.Daft et al., "Beam Profiles and Images from Two–Dimensional Arrays", Ultrasonics Symposium, 1990, p. 775.

Marshall T. Robinson and Olaf T. von Ramm, "Real–Time Angular Scatter Imaging System for Improved Tissue Contrast in Diagnostic Ultrasound Images", IEEE Trans. on Ultrasonics, Ferroeletrics and Frequency Control, vol. 41, No. 1, Jan. 1994.

S.W.Smith et al., "Two–Dimensional Arrays for Medical Ultrasound", Ultrasonics Symposium, 1991, p. 625.

Richard E.Davidsen and Stephen W.Smith, "Sparse Geometries for Two–Dimensional Array Transducers in Volumetric Imaging" Ultrasonics Symposium, 1993, p. 1091.

*Primary Examiner*—Francis Jaworski

[57] ABSTRACT

This invention employs an ultrasound apparatus with a phased transducer having transmit and receive array systems to form an electronically scanned ultrasonic "pencil" beam (25) from crossed flat acoustic beams. The flat transmit beams and flat receive apertures are shaped by the arrays with size of individual elements on the order of the wavelength of a generated carrier frequency in a human body. The separation of array functions in the transmission and reception modes reducess the side lobe level and improves the noise performance. A fast method of acquisition of two dimensional images is described. This method uses a property of a dynamic focused and scanned flat acoustic beam together with the ability to shape flat synthetic receive apertures from digitized and memorized amplitude information. The same fast method of three dimensional image reconstruction is suggested, which uses an unfocused acoustic beam generated by a single transducer element together with the ability to form flat synthetic receive apertures in memory.

24 Claims, 15 Drawing Sheets

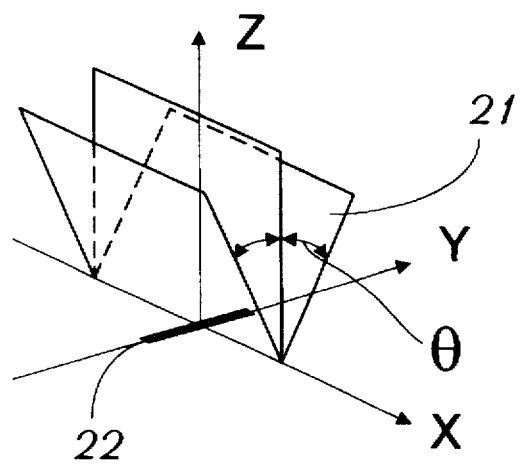
*Figure 1.a*
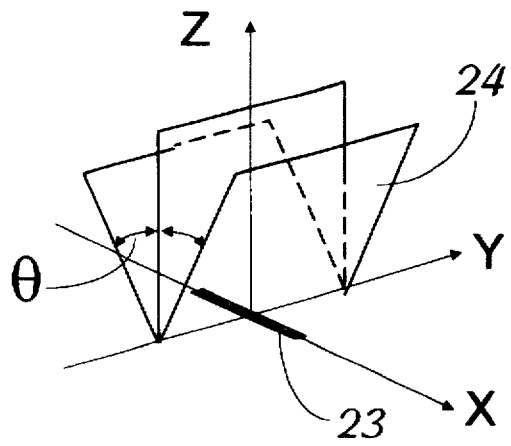
*Figure 1.b*
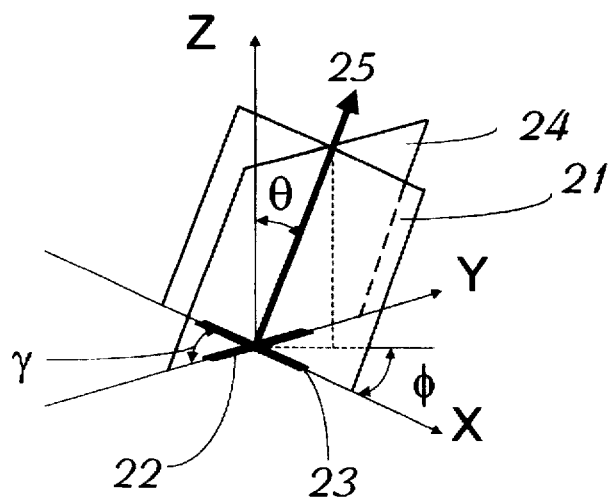
*Figure 1.c*

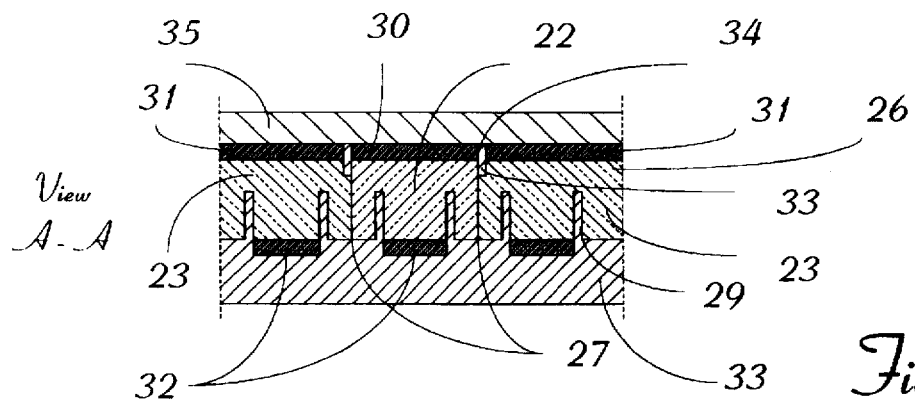
Figure 2.b
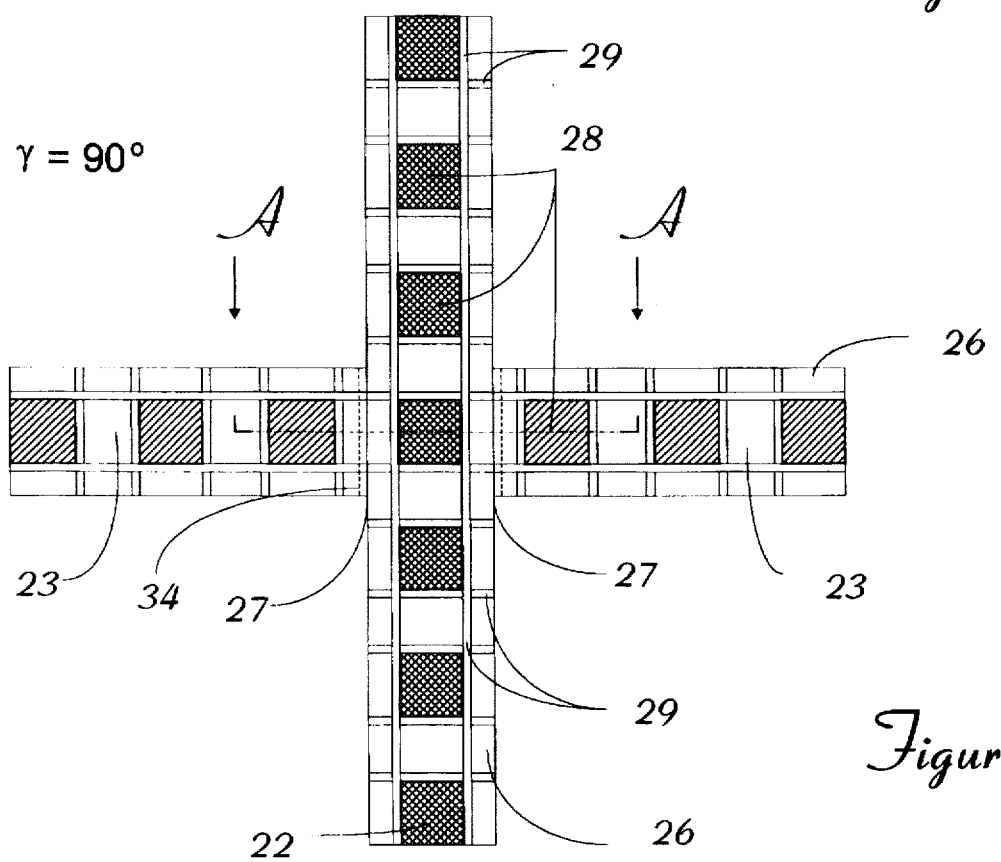
Figure 2.a

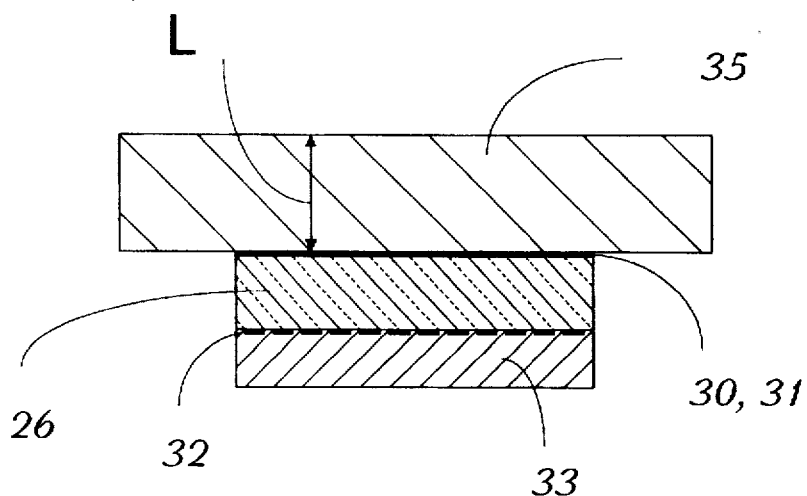
Figure 10.a
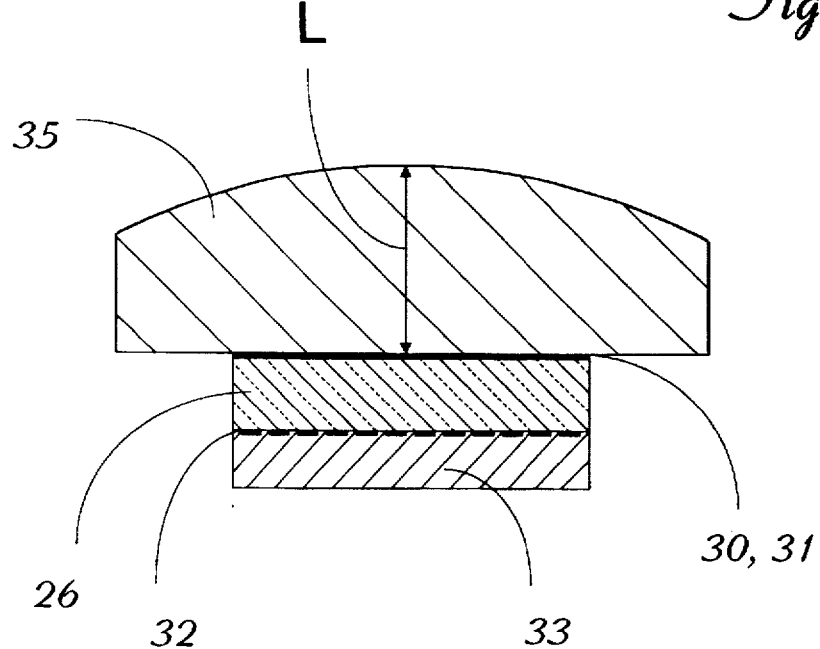
Figure 10.b

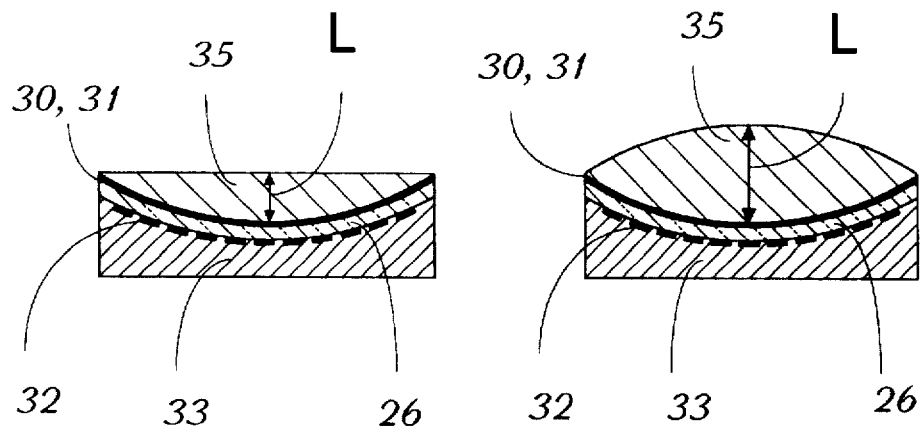
Figure 10.c
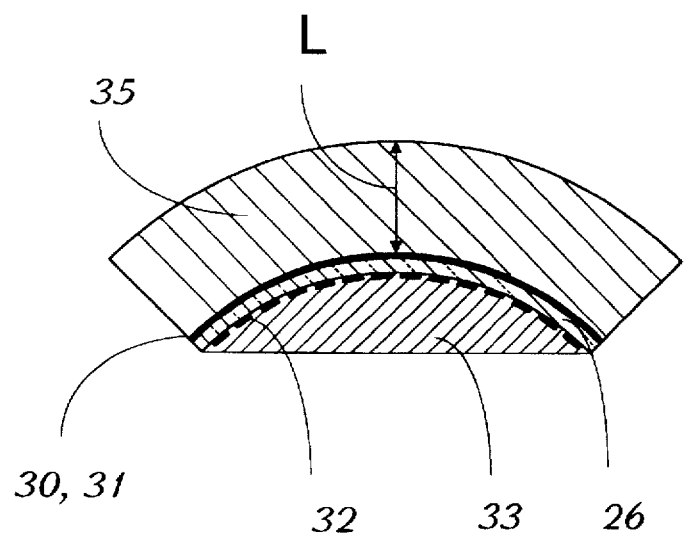
Figure 10.d

ULTRASOUND APPARATUS FOR THREE DIMENSIONAL IMAGE RECONSTRUCTION

DESCRIPTION

1. Field of the invention

The present invention relates to the apparatus for three dimensional investigations of human body structures. More precisely, the invention relates to a cross transducer, which allows transmission and reception of electronically scanned acoustic beams and three dimensional reconstruction of time-critical anatomical images.

2. State of the Art

Methods and apparatus have been devised for the three dimensional ultrasound reconstruction of human body structures by the acquisition of two dimensional images, which after analysis are reconstructed into three dimensional images.

U.S. Pat. No. 5,159,931 of Riccardo Pini discloses an ultrasound apparatus which obtains three dimensional images by mechanical rotation of a linear array transducer, which receives two dimensional images at known angles. It reconstructs the three dimensional images of the anatomic structures.

However, for the acquisition of the two dimensional images which will be used for reconstruction of the three dimensional images the usual linear and sector scan transducer arrays are suggested. This means, in the best case, a transducer with mechanical elevation focusing is used and the resolution for registered two dimensional images will be strongly limited because the beam size in the elevation coordinate permits good quality reception only in the vicinity of the focal point.

Another method for collecting three dimensional images described in the same patent is the use of a matrix transducer or, at least, a simple cross transducer which consists of two orthogonally placed arrays which can be scanned electronically. It is possible to obtain good resolution for both, lateral and elevation coordinates. However, it requires the use of all individual elements of the matrix.

S. W. Smith et. al. describe the experiments with a 16×16 matrix transducer (S. W. Smith, G. E. Trahey and O. T. von Ramm, TWO-DIMENSIONAL ARRAYS FOR MEDICAL ULTRASOUND, ULTRASONIC SYMPOSIUM, 1991, p.625). 96 transducer elements are used for shaping the transmit acoustic beam and 32 transducer elements are used for reception of the echo signals in a cross form, which consists of two 16 element linear arrays. For each 16 element array used for reception of the echo signals, 8 elements are used as transmit and receive elements simultaneously, and 8 are used for receive echo signals only.

The cross transducer utilizes a small number of channels, however, when the transducer array elements are used as transmit and receive channels simultaneously (even if they are used in this mode partially as in the second reference) it produces high levels of side lobes.

Therefore, it is possible to realize such a probe for three dimensional imaging, for example, the matrix form transducer. However, good image quality requires both high resolution along the lateral and elevation coordinates and the simultaneous low level of side lobes. Realization of these conditions leads to the large number of individual transducer elements in the matrix array and, respectively, a large number of electronic channels. The number of channels N in this case is $$N = n\ col * n\ row,$$

where n col and n row are the number of the elements in the columns or rows of the matrix transducer.

Good quality of the acoustic beam requires at least 40–50 (more is better) elements in the columns and rows, and the total number of channels for the matrix becomes very large.

Three dimensional images are formed from registered two dimensional images which are formed from a set of separate acoustic lines. Every acoustic line is constructed from multiple transmit zones and requires multiple transmit pulses equal to the number of focal zones. Therefore, the time for acquisition of the three dimensional image T3d is $$T3d=T2d*N2d \text{ for } T2d=(NAL*NF*TAL)$$

where T2d is a time of the two dimensional image registration, N2d is the number of the two dimensional images necessary for the formation of a three dimensional image. NAL is the number of acoustic lines necessary for the formation of a two dimensional image. NF is the number of transmit focal points for every acoustic line and TAL is the registration time of one acoustic line and is approximately equal to (100–150)µsec for a 7.5 MHz probe. For NPF=8, NAL=200 and N2d=200 we obtain T3d=(32–48)sec. Some rejection of T2d can be obtained by the shortening of the TAL for focal points placed near the surface of probe. It allows to reject T2d approximately by a factor of 2. Even accounting for this condition, T2d is substantial. So, the acquisition of three dimensional images is a problem even for electronically scanned transducers. The use of a mechanically rotated probe increases this time significantly.

SUMMARY OF INVENTION

The goal of the present invention is to receive approximately the same characteristics of the acoustic beam as for a matrix transducer, while using a reasonable total number of individual elements and a reasonable number of electronic channels. The concept of the crossed flat acoustic beams for shaping of the "pencil" beam is used. The ability to shape the acoustic beam for any array depends on the radiation directivity and the number of individual elements used in this array. For shaping a flat acoustic beam, the size of the individual array elements along the direction of the normal to the placement of the array should be small. According to the invention herein presented, the separate phased array systems are used for radiation of the acoustic wave package and for reception of the echo signals. This step reduces the level of the side lobes sufficiently and improves the noise performance. Crossed flat beams can be created by the use of a cross geometry in the placement of the arrays, which should have axial symmetry. It should also have the same origin center for transmit and receive arrays and should have at least one or more transmit arrays and one or more receive arrays axially symmetric and oriented relative to each other at an optimal angle γ. The optimal angle γ between the plurality of the transmit and receive arrays is $$\gamma = \frac{\pi}{(n_{tr} + n_{rec})}$$

where $n_{tr}$ is the number of transmit array individual elements and $n_{rac}$ is number of receive array individual elements.

This formula shows the optimal angle for obtaining the same resolution along lateral and elevation coordinates. Angle and placement of the transmit and receive arrays can be changed to obtain better resolution along lateral coordinates by sacrificing the elevation resolution.

Total number of transducer elements and electronic channels Ncr for this scheme is $$Ncr=ntr*l+nrec*m,$$

where l and m are the number of the individual elements in the transmit and receive arrays.

Comparison of this formula with the formula for the matrix transducer above shows that Ncr is sufficiently less than the number of channels N for the matrix transducer and produces approximately the same quality of the shaped acoustic beam.

The use of a cross transducer with one transmit array opens the possibility of reducing the acquisition time of the two dimensional images and accordingly the three dimensional image acquisition time also. It is defined by the property of the flat acoustic beam, shaped by one transducer array. The flat beam has no definite focal point in space. An acoustic beam focused at some focal distance determines the adjusted aperture, while the focal distance is distributed in space along some angle sector. If information registered by the electronic channel of the individual element of the receive array is digitized and recorded in some memory ("digital beamformer schematic"), we can adjust any number of the acoustic lines into an angle sector by shifting the recorded individual elements information by a predetermined number of digits which imitate the delays necessary to establish the receive aperture. One acoustic pulse is required for registration of a part of the two dimensional image at one focal distance into the investigated angle sector. The number of acoustic pulses required for registration of the complete two dimensional image is equal to the number of transmit focal distances NF. A device such as a cross transducer with one transmit and one or more receive arrays joined with a digital beamformer schematic reduces the two dimensional image registration time by a factor of approximately equal to NAL. Besides, such a scheme reduces the acoustic radiation dose upon the human body by the same factor. This point is an important feature of the present invention.

Additional reduction of the three dimensional image registration time can be obtained by the use of an ultrasound apparatus with a transducer having one individual transmit element and a receive array system providing a fast reconstruction of three dimensional images. The apparatus comprises one transmit transducer placed at the center of the axially symmetric receive array system having a plurality of the receive arrays shifted from each other at an optimal angle γ. The transmit transducer emits an unfocused acoustic beam into some solid angle defined by the size of the transducer. The receive array system has the number of receive arrays necessary to obtain the dynamically focused and scanned receive "pencil" aperture. The number of receive arrays should be enough to provide a satisfactory level of side lobes. The first way of side lobe rejection is absent in this case, when the transmit beam is shaped by the transmit aperture. The rejection of side lobes may be achieved by shaping of the receive aperture only which is known as the second way. So, a satisfactory level of side lobes should be provided only by the receive array system with the increase in the number of receive arrays. Individual elements of receive arrays are connected to an apparatus the same as written above. Received echo signals are amplified and digitized for each individual receive element and subsequently stored in memory. The shaping of the acoustic lines is provided by a fast algorithm comprising the shifting of the digital information for a predetermined number of digits providing the scanned and focused synthetic apertures and the selection of the predetermined focal point into the irradiated solid angle, summation of the individual element's amplitude information in time is used to create each separate acoustic line which is then used to reconstruct the two and three dimensional images. In this case, the number of individual elements in the receive array system and the number of channels for time and amplitude analysis of the received information increases in contrast with the schematics described above. But, this increase allows the registration of a single three dimensional image with one radiated acoustic pulse. Besides this, the level of the radiated acoustic power is reduced significantly and such acoustic apparatus becomes less harmful than any system used previously to investigate the human body.

BRIEF DESCRIPTION OF THE DRAWINGS

These features and advantages of the present invention will be better seen by reference to the detail description with accompanying drawings wherein:

FIG. 1a shows the principle of obtaining an acoustic beam scan in the YZ plane.

FIG. 1b shows the possibility to scan the acoustic beam in the XZ plane.

FIG. 1c shows the principle of the shaping of the "pencil" beam by crossing of the two flat beams.

FIG. 2a presents the exemplary drawing of a transducer composed of one transmit and one receive linear array.

FIG. 2b shows the cross-section of the central part of the transducer shown in FIG. 2a FIG. 3 shows the view of the transducer with one transmit and one receive linear array manufactured upon the common square piezoelectric plane.

FIG. 10a shows the cross section of the flat transducer with increased flat impedance matching spacer.

FIG. 10b shows the view of the flat transducer with increased impedance matching spacer having the spherical front surface.

FIG. 10c shows two exemplary views of the concave cross transducer with increased impedance matching spacer.

FIG. 10d shows the view of the convex cross transducer with increased impedance matching spacer.

DETAILED DESCRIPTION

Figure 3:
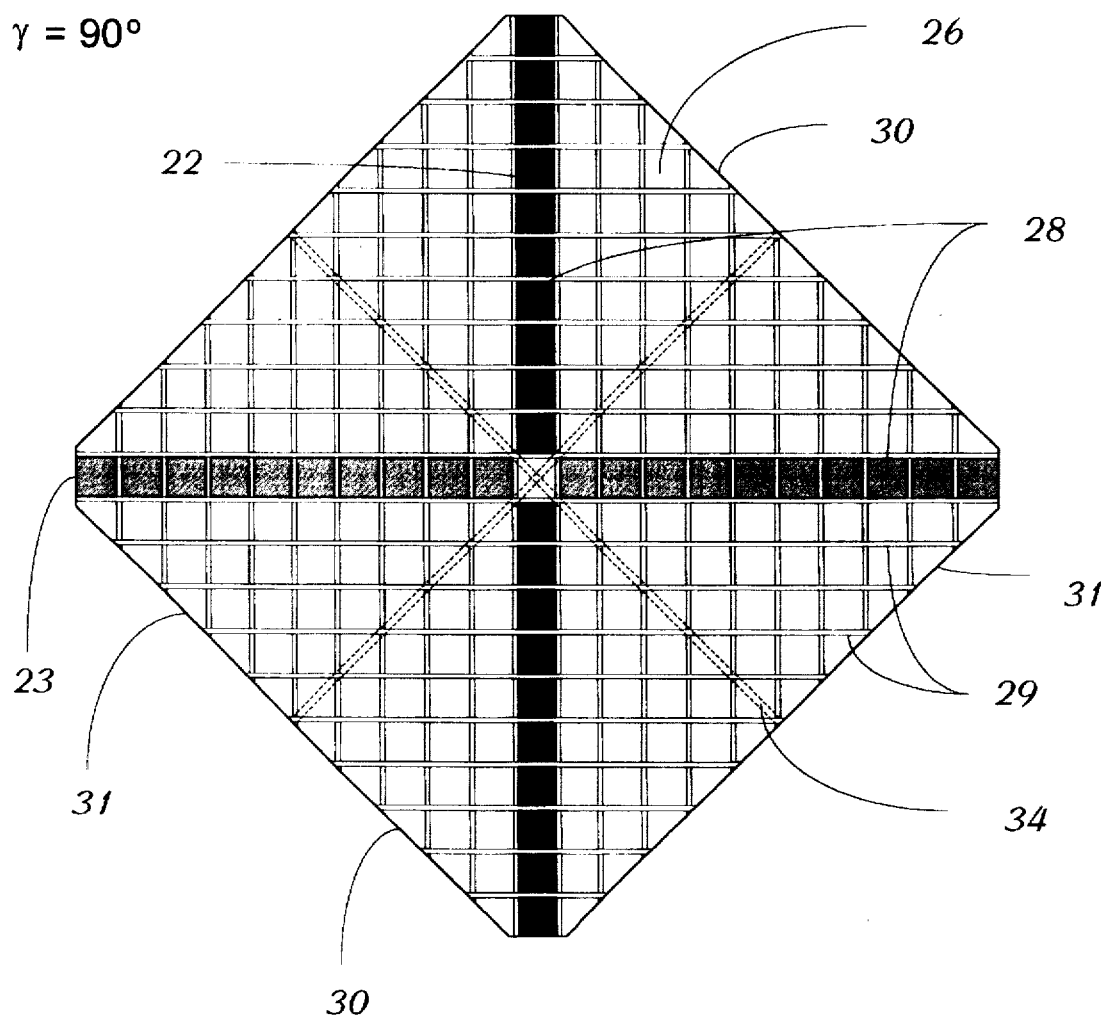

As it was written above, the conception of the flat crossed beams produced by the transducer arrays is used in the present invention. FIG. 1a shows the principle of scanning of the flat acoustic beam 21 generated by the linear array 22 (transmit array). The scan and dynamic focusing of the beam is produced by the adjustment of the delays of the pulse generators which drive the transmit array individual elements. Reception of the signals is done the same way (see FIG. 1b) by another transducer array 23 (receive array), which has axial symmetry with array 22 and is turned relative to the transmit array 22 at the angle γ. Receive transducer array 23 provides a reception of the echo signals and has a flat aperture 24. FIG. 1c illustrates the process of the creation of the "pencil" acoustic beam 25 by crossing of the flat beams 21 and 24. The optimal angle for the transducer with one transmit and one receive array is equal to 90°. Transmit array 22 and receive array 23 form the transmit and receive systems which are separated from each other including the separate ground electrodes. The number of the arrays used in the transmit and receive system can be more than one. In this instance, the optimal angle is changed and can be calculated from the formula above. The choice of such a value for the optimal angle is defined by the level of side lobes generated by the transducer. The level of side lobes increases smoothly with decrease of the angle,) increases very sharply after γ=γlim and achieves the maximum for γ=0° (This is the usual schematic when a linear array is used as transmit and receive arrays simultaneously). The value of the limit angle γlim depends on the number and pitch of the individual elements used to form the transducer arrays and, for example, a transducer with two transmit and two receive linear arrays is equal to γlim=10°.

The Table 1 shows the results of the calculation of the side lobe level for the case of a 7.5 MHz cross transducer with two transmit and two receive arrays, with 64 individual elements at a pitch of 0.25 mm, and at a 5 mm distance from the acoustic beam with angular dependence on y between transmit and receive systems (We use a non-steered beam, θ=0°, φ=0° and focal distance F=20 mm).

TABLE 1

| γ (degree) | Side lobe level (dB) |
| --- | --- |
| 0 | −14.6 |
| 10 | −35.7 |
| 20 | −39.7 |
| 30 | −41.2 |
| 40 | −43.7 |
| 45 | −44.1 |

Additionally, the view of the side lobe map is not uniform. It has sharp peaks which repeat the shape of the flat beams formed by the different arrays of the transmit and receive systems. The values shown in Table 1 correspond to the maximal values of the side lobe peaks normalized to the intensity of the main beam lobe for the central point with coordinate 0 mm. The level of the side lobes between the peaks is sufficiently lower and achieves a value of −70 dB approximately.

The possibility to separate the ground electrodes of the transmit and receive system is an important advantage of the present invention (at least, separation of analog receive inputs from the digital parts, in particular the transmit part). The noise from the output of the analog part of the apparatus consists of two main components: a random component and systematical component. The random component includes the noise of the transducer, and elements of the analog schematic where main noise is the noise of the first transistor used for amplification of the echo signals. The systematical component exceeds the random components sufficiently and is defined by the field and ground couplings between the transmit and input receive parts of the apparatus. The ground coupling is determined by the common ground between transmit and receive systems, and gives the main contribution to the output noise level.

The separation of the transmit and receive ground electrodes is relative. Any electronic device must have the common ground electrode, but the level of interference of one part of the apparatus upon other parts depends on the connection scheme of the ground electrodes of the different parts of the device. So, when we use the term "separate ground electrode" it means this part of apparatus has a separate ground electrode joined with common ground electrode of the acoustic machine in one point.

So, accordingly the present invention, transmit and receive array systems have to be separated completely including the ground electrodes. This step will realize a low level of side lobes by increasing the second way efficiency, and improve the noise performance.

An exemplary view of the transducer with one transmit and one receive linear array and for γ=90° is shown in FIG. 2a. The transducer contains three rectangular strip plates of the piezo electric material 26. One of them is used for manufacture of the transmit array 22, two others form the arms of the linear receive array 23 by gluing 27 to the center of the transmit array 22. Elements 28 of the arrays have a square shape and are formed by the cutting of the grooves 29 in the piezo electric substrate plates 26.

The cross-section of the central part of transducer is shown in the FIG. 2b. Transducer assembly comprises a piezo electric layer 22 and 23 (see FIG. 2b) which has ground electrodes 30 and 31 and separate signal electrodes 32 placed upon the opposite side of the piezo electric layer. The grooves 29 are cut upon the signal layer side to produce individual elements of transmit and receive arrays. Isolation substance 33 is filled into grooves and forms the isolation layer.

The opposite side of the piezo electric layer 26 has ground electrodes. Electrode 30 is a ground electrode of the transmit array. Electrodes 31 are ground electrodes of the receive array, separated and isolated from ground electrode 30 of the transmit array 22 by grooves 34 cut along the ends of the piezo electric plates used for manufacture of the receive array 23 and filled with the isolation substance 33. The front side of the transducer is screened by an impedance matching layer 35 used for emitting the acoustic wave package into the investigated part of the human body and matching the acoustic impedance between the human body and the piezo electric layer.

Signal electrodes 32 are connected with transmit and receive parts of the apparatus by the cable wiring.

FIG. 3 shows another view of the transducer with one transmit and one receive linear array. Piezo electric layer 26 has a square shape and transmit 22 and receive 23 arrays are placed along diagonals of the square. Elements 28 of the transmit and receive arrays are formed by cutting the grooves 29 on one side of the piezo electric layer 26. Ground electrodes of the transmit and receive system are placed on the opposite side of layer 26 and separated from each other by grooves 34 as is shown in FIG. 3. The pairs of the ground electrodes 30 and 31 are joined by the external subsequent mounting. An impedance matching layer placed on the ground electrode side, as is done with transducer of FIG. 2.

Figure 4:
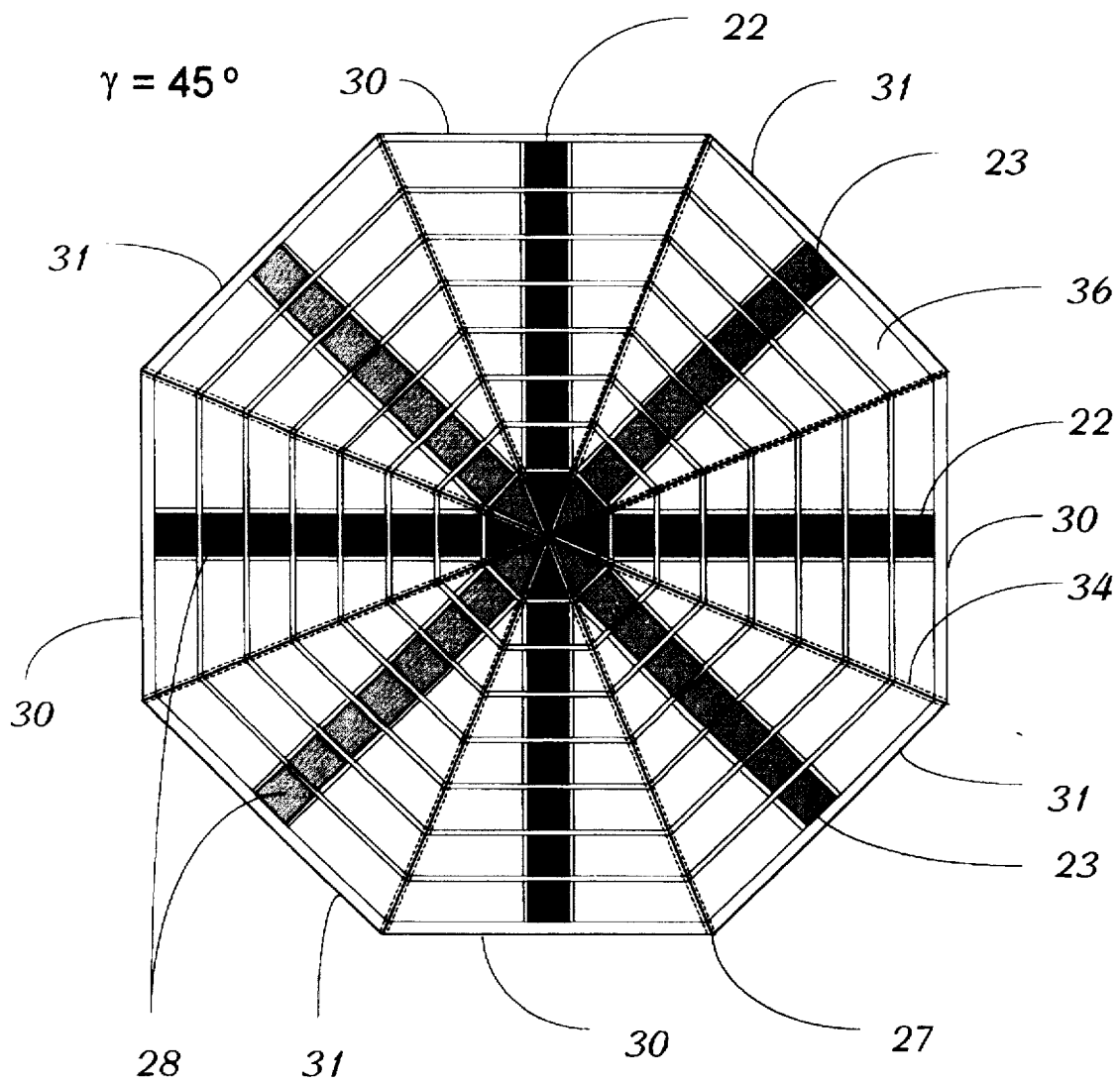
FIG. 4 shows the transducer with two transmit and two receive linear arrays composed from the sectors of the piezoelectric material.

FIG. 4 presents the exemplary view of the transducer which has two transmit 22 and two receive 23 arrays. The angle γ in this instance is equal to 45°. The transducer is formed from separate sectors 36 of the piezo electric material adhered to each other after manufacture of the individual elements of the linear arrays. The form of the individual elements 28 of arrays is made by the cut of the grooves 29 in the sectors 36 of the piezo electric material 26. The ground electrodes 30 and 31 of the transmit and receive array system are placed on the opposite side of the sectors 36 and separated from each other by grooves 34 and are cut along the adhered sides 27 of the sectors 36. Common ground electrode of the transmit array system is formed by the external joining of the electrodes 30 and the common ground electrode of the receive array system is formed by the external joining of the electrodes 31. The connection of individual elements 28 with subsequent apparatus is made by the cable wiring.

Figure 5:
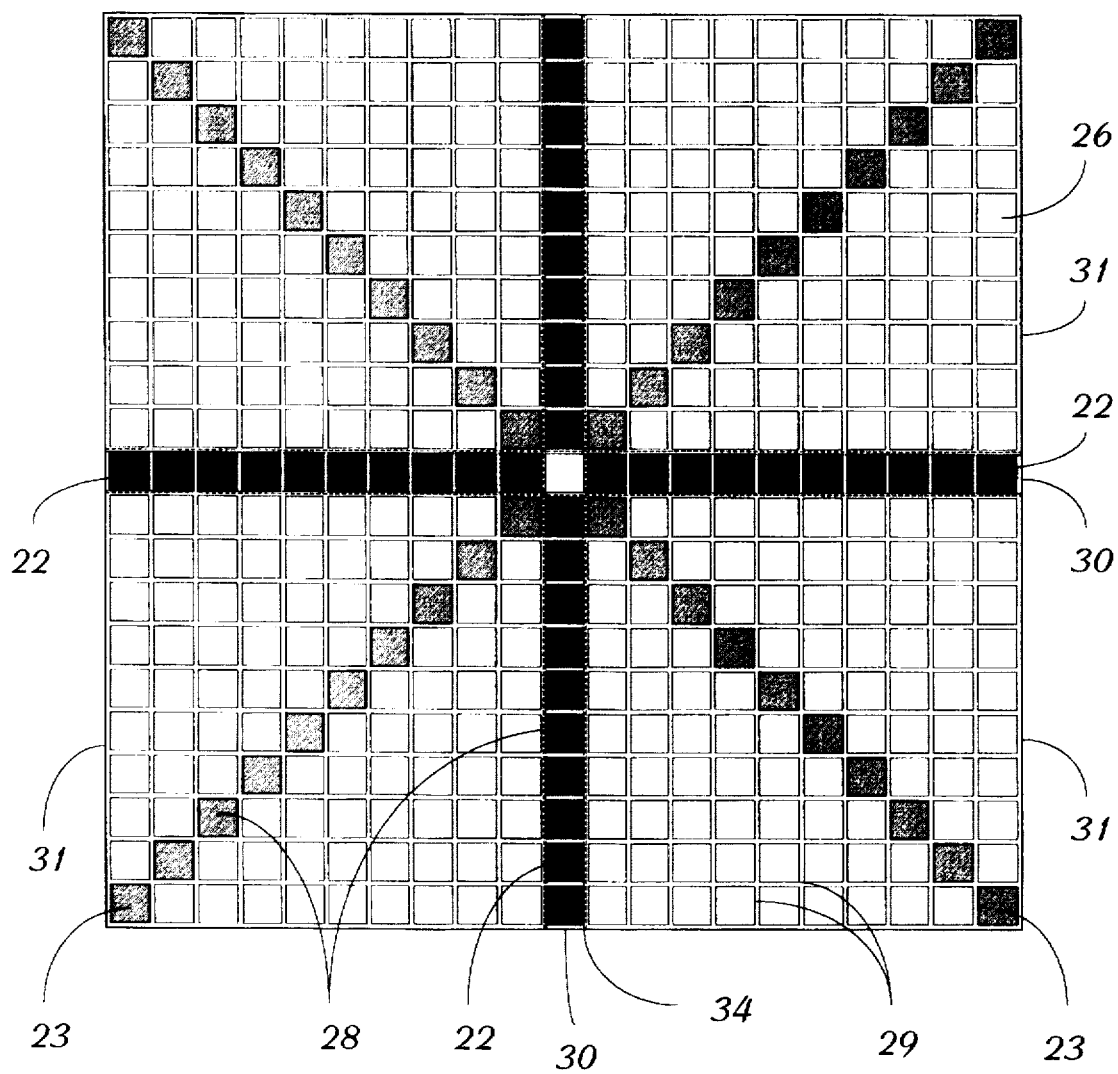
FIG. 5 shows the view of the transducer with two transmit and two receive linear arrays manufactured by the same method used to create the matrix transducer.

Another plan of the transducer with the angle γ=45° and transmit and receive systems contain two arrays for each system as shown in FIG. 5. The method of manufacture of this transducer version is the same as the matrix transducer manufacture, which has an odd number of columns and rows. The piezo electric substrate plate 26 has a square shape. The transmit arrays 22 are placed along the central column and central line of the matrix. The receive arrays 23 are placed along the diagonals of the matrix. The pitch of the individual elements of the transmit and receive arrays is different by a coefficient equal to √2. This difference influences the width of the acoustic beam intensity distribution along the investigated depth (coordinate Z) and reduces it. It is admissible for the receive system, because usually the size of the receive zones of the image is less than the size of the transmit zones. Individual elements 28 of the transmit 22 and receive 23 arrays are separated by the grooves 29. The ground electrodes 31 and 30 are placed on the opposite side of the piezo electric plate 26 and separated by the grooves 34 and are cut along both sides of the transmit arrays 22. Every individual element signal electrode of the transducer arrays connects with the subsequent apparatus by a separate cable, the ground electrodes 30 of the transmit and electrodes 31 of the receive systems are joined by the external mounting.

Figure 6:
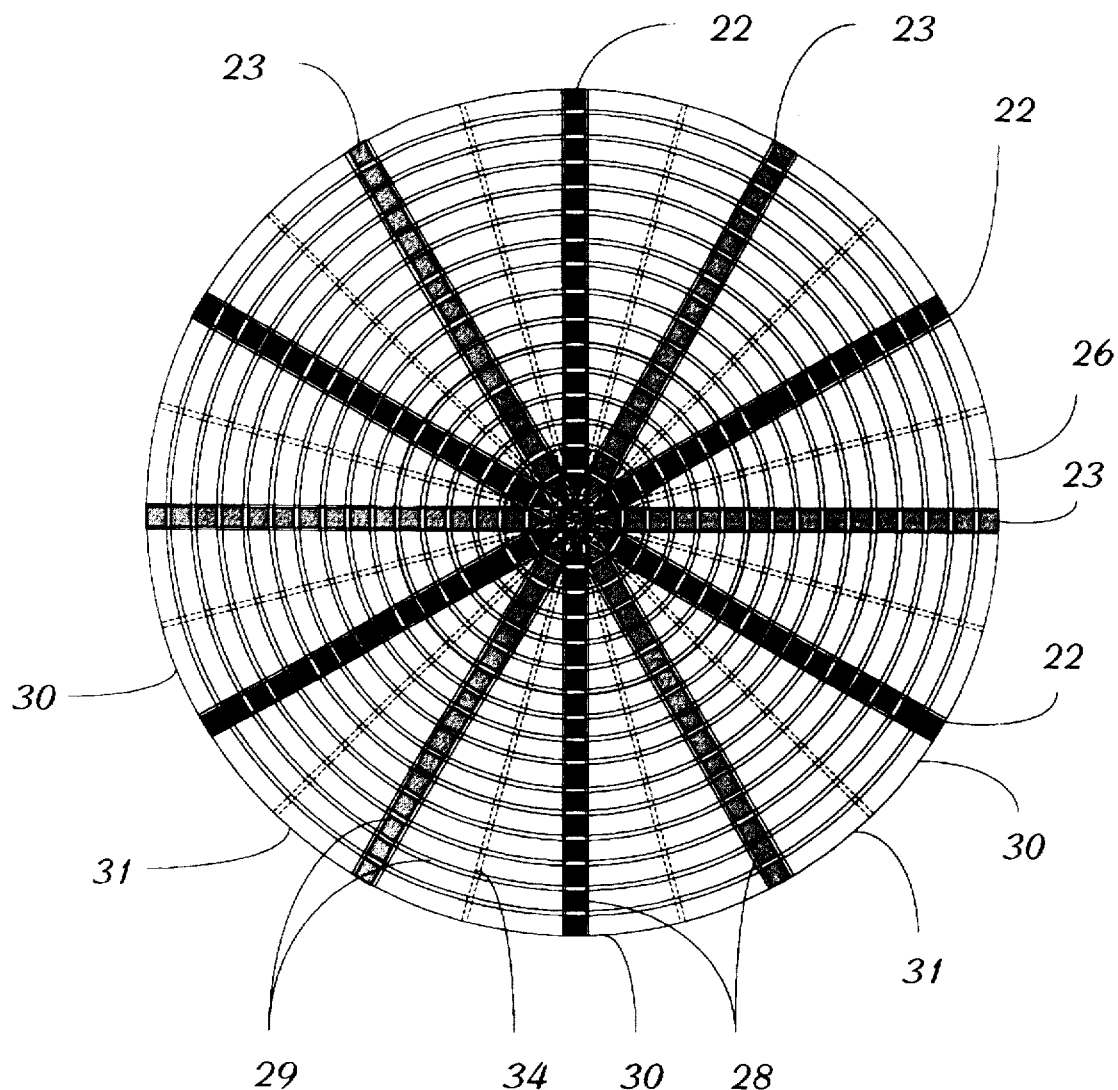
FIG. 6 shows the view of the transducer with three transmit and three receive linear arrays manufactured upon a disk of piezoelectric material.

The view of the transducer with three transmit 22 and three receive 23 arrays and made on the disk piezo electric plate is presented in FIG. 6. The angle γ for this version of the transducer is equal to 30°. The manufacture of the individual elements 28 of arrays 22 and 23 is produced by cutting the circular and radial grooves 29. Separation of the transmit 30 and receive 31 ground electrodes on the opposite side of the piezo electric disk is done by cutting the radial grooves 34. Connection of the individual element signal electrodes with apparatus is produced by the cable wiring. Ground electrodes are joined by the external mounting and form the separate transmit and receive ground electrodes.

As it was stated above, for a transducer with two transmit and two receive arrays, the amplitude of side lobes begins to increase sharply for angle γ<10°. This limit is valid for a calculated length of the arrays which consists of 64 individual elements placed with pitch equal to 0.25 mm, the size of the individual elements is equal to 0.1 mm with a frequency of 7.5 MHz, which will be changed for a different set of parameters. It means that a limited number of transducer arrays (equal to 18) can be used for shaping of the "pencil" beam in this case. The number of individual channels is quite high in this case, but even for such a case, the total number of channels is approximately three times less than the number of channels for the matrix transducer with the same number of individual elements for columns and rows.

Figure 7:
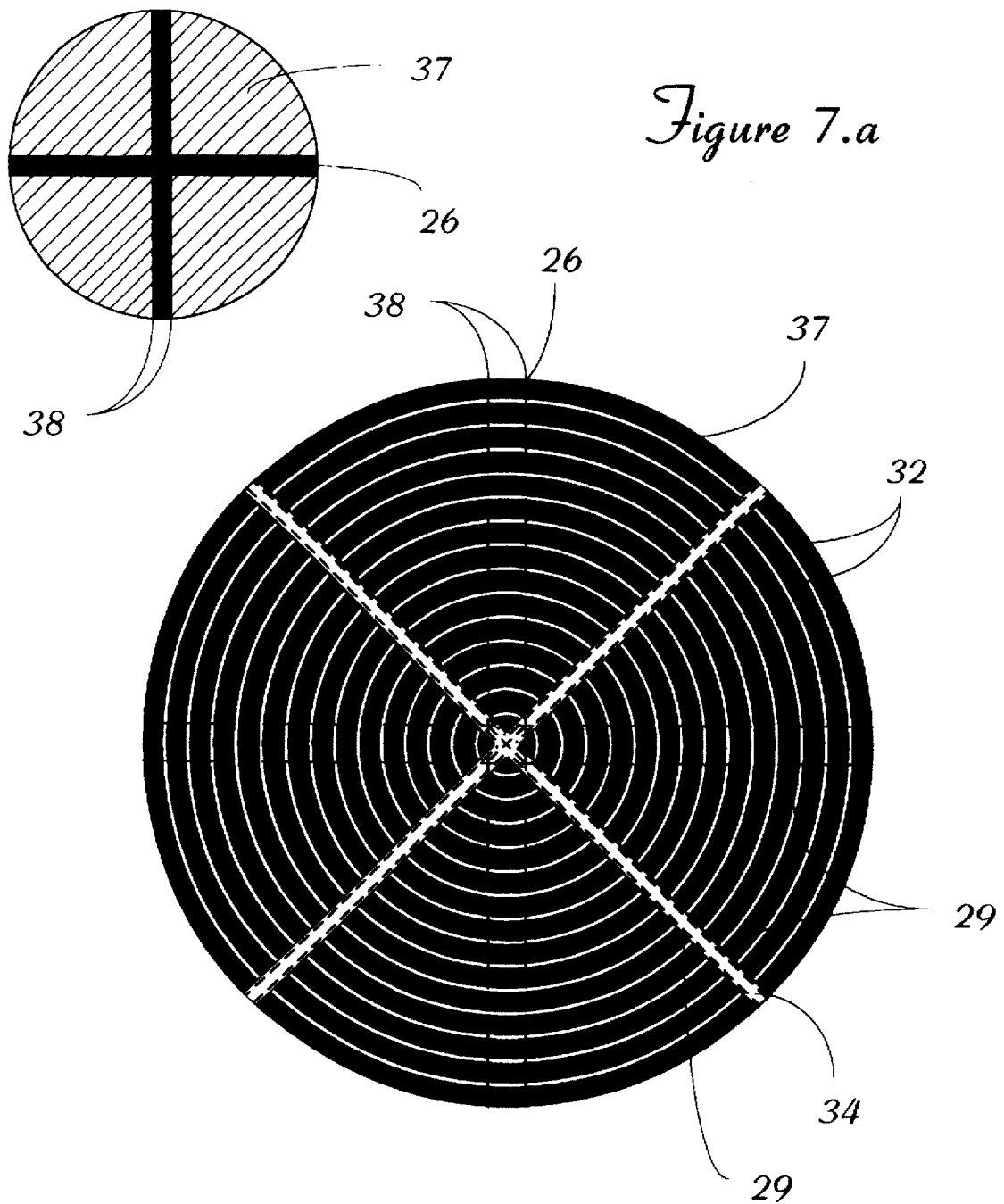
FIG. 7a shows the view of the composite material wafer.
FIG. 7b shows the view of a transducer having an increased surface of the individual element signal electrodes manufactured upon the composite material disk.

One of the problems of manufacturing the transducer designs shown in the FIGS. 2–6 is the small size of the individual element signal electrodes. This makes it difficult to connect with subsequent apparatus. It is necessary to develop and increase the area of the signal electrodes which are used as contact pads for the connection with the subsequent apparatus. The view of the transducer version with increased area of the contact pads is shown in the FIG. 7a and 7b. Thin plates of the piezo electric material 26 are placed between the sectors of the non-piezo electric material 37. The connection of the plates 26 and sectors 37 depends on the properties of the non-piezoelectric sector substrate and can be done by heat or chemical or another treatment which can provide a reliable connection between these parts (see FIG. 7a) and receive the distinct boundaries 38 between piezo and non-piezo electric material parts 26 and 37 without the violation of the thickness of the piezo electric material plate 26. After polish and metallization of both sides of the wafer the individual element signal electrodes 32 are formed by the circular and radial grooves 29. The ground electrodes of the transmit and receive system are formed by the cut of grooves placed on the opposite side of the wafer (see FIG. 7b). As shown, the area of the contact pads 32 is increased sufficiently.

If fiberglass is used as non-piezo electric material 37, the first stage of the signal and ground electrodes shaping and wiring can be done by the same methods as for printed circuit boards.

As it was written above, the ability to scan the acoustic beam for this kind of transducer depends on the ability to shape a flat beam by the single array and, in the first place, by the radiation directivity of the individual elements of the transducer arrays. The individual pointed element with elementary dipole directivity of radiation is the best decision in this instance. But, even in this case, the maximal scan angle will also be required. Negative influence of the individual element directivity of radiation can be decreased by the same method used for usual transducers, namely, use of the curved shape of the transducer.

Figure 8:
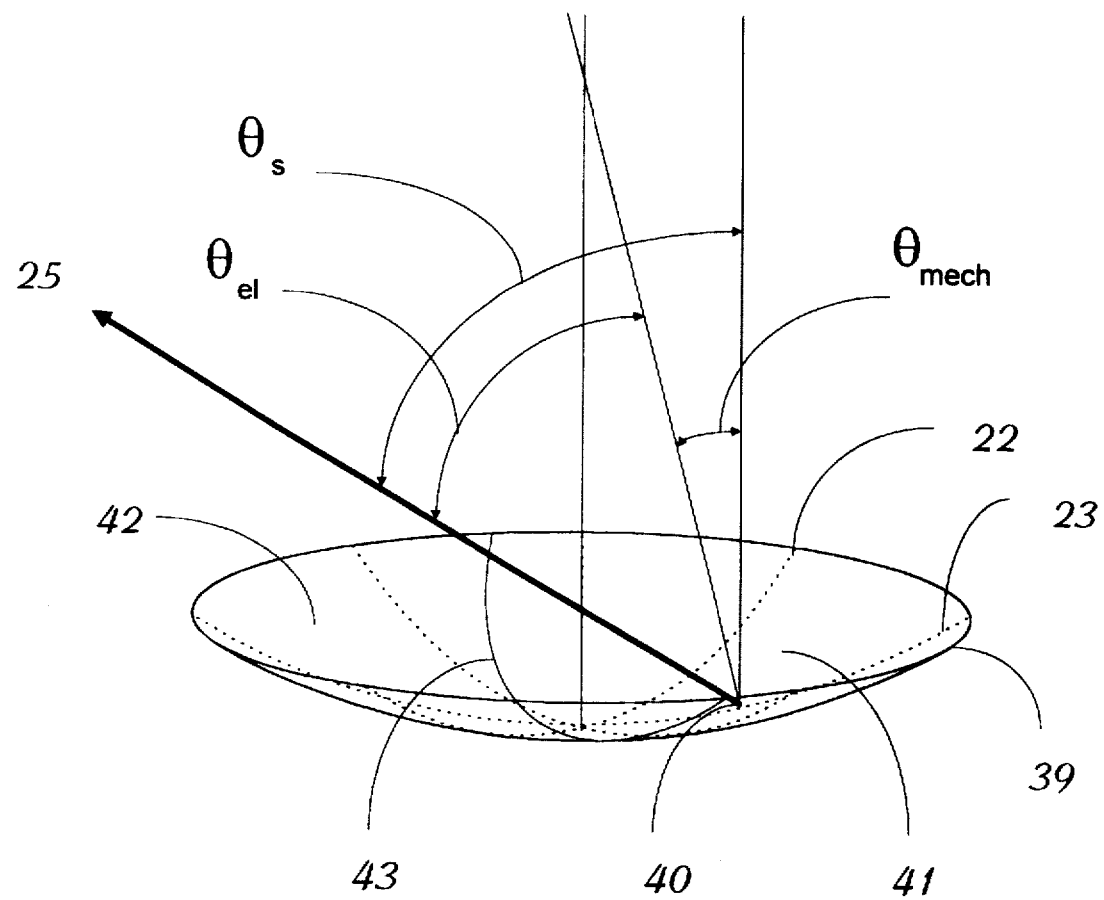
FIG. 8 shows the sketch of the concave cross transducer.
Figure 9:
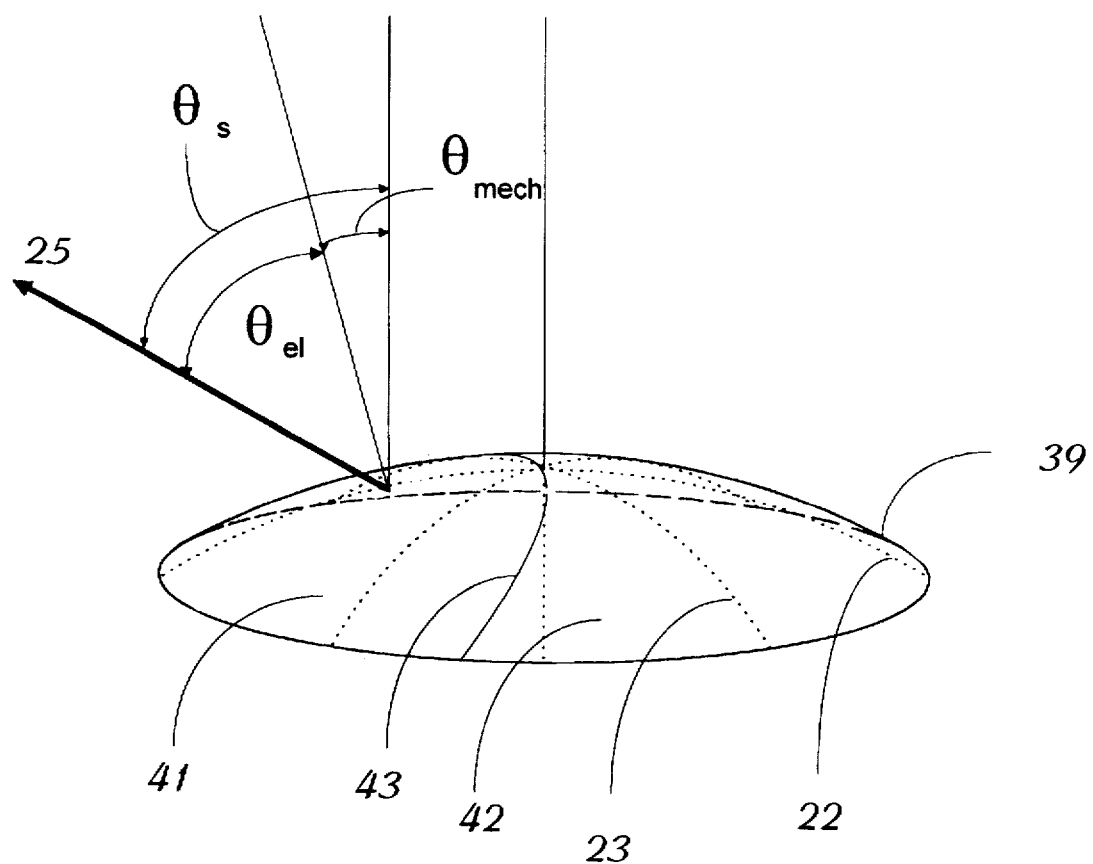
FIG. 9 shows the sketch of the convex cross transducer.

The exemplary views of the curved transducer design are shown in the FIGS. 8 and 9. FIG. 8 presents the schematic version of the concave cross transducer. The body 39 of transducer can be manufactured from piezo electric or composite material. The concavity of the body 39 can have the shape described by any symmetrical function, for example, spherical. The transmit 22 and receive 23 array systems are manufactured in such a way that the ground electrodes are placed on the concave side of the body and individual element signal electrodes are shaped on the opposite surface of the transducer body. The conceived surface of the transducer has the impedance matching layer used for the acoustic contact with the investigated object. As shown from FIG. 8, scan angle θs for this version is increased for angle θ mech by the mechanical turn of the individual elements and is $$\theta_s = \theta_{el} + \theta_{mech}$$

where θel is the scan angle defined by the electronics. The schematic of the pulse driver and reception apparatus should have switches for changing the order and number of the individual elements which can be turned on in the transmit and receive apertures of acoustic line 25. Individual elements of arrays which cannot participate in the shaping of the beam effectively should be turned off. It is shown schematically in FIG. 8 where the origin point of the acoustic beam 25 is shifted to the point 40. It is done by the definition of the working space 41 and turning on of the individual elements of transmit and receive arrays in this area electronically. The individual elements of the arrays which are placed in area 42 cannot contribute in the shaping of the acoustic beam in the Al direction effectively and are turned off. The line 43 shows the boundary between the working space 41 and shadow area 42.

The concave cross transducer design is more complex in the manufacture than the flat version, it requires the use of more individual elements for transmit and receive arrays, but increases the possible scan angle, reduces the dynamic range of delays used for dynamic focusing and phase adjustment of the individual elements of arrays in the pulse driver and reception apparatus and increases the size of the individual elements and radiated acoustic power respectively. The condition of axial symmetry is violated for the apertures shifted from the center of the transducer. However, in this case, it is possible to receive the crossing of all flat beams at the same focal point.

Another method which increases the scan ability of the transducer is the use of the convex shape of the probe. FIG. 9 shows exemplary sketch of the transducer with transmit 22 and receive 23 array placement on the convex shaped body 39. As shown in the figure, the total scan angle θs is increased for the angle θmech also. For acoustic line 25 with origin point 40, the transducer has the working space 41 where individual elements of transmit and receive arrays are turned on and provide the shaping of the acoustic line 25 in this direction. The line 43 shows the boundary between the working space area 41 and the shadow area 42 where individual elements of arrays are turned off. In contradiction with the concave shape of the transducer which turns the surface of the individual elements of arrays in the direction of the acoustic line, convex shape turns the individual element surfaces in the opposite direction away from the acoustic line. The working space 41 is less than the working space for the concave transducer, the number of individual elements used for forming the necessary apertures is less also and, consequently, the resolution of this kind of transducer is lower. The opposite direction turn of the individual elements imposes harder requirements to the directivity of radiation and size of the individual elements of arrays than for the flat transducer, but the shape of the probe is very convenient and can be used in some applications.

One of the important requirements for transducers used for investigation of disease near the surface of the skin is the ability to provide the dynamic focusing of the acoustic beam and high resolution at a small distance from the surface of the probe. It is difficult to satisfy this requirement because of the usual optic relations between the size of the aperture, number and pitch of the turned on individual elements, size of the possible investigated zone along the depth and width of the beam. This problem is very important for design of the transducers described above, especially for the flat transducer which has a fixed origin for all acoustic lines and a limited sector of the beam scanning. On the other hand, in any design of the acoustic probes, the impedance matching layer is used for termination of the impedance of the piezo electric material of the probe and the impedance of the human body. But usually, the thickness of this layer is very small to provide the focal distances near the surface of probe.

It is desirable to use the impedance matching layer to provide the dynamic focusing of the acoustic beam and high resolution at a small distance from the surface of probe, giving simultaneously to it the additional-function of the transparent acoustic spacer which provides the stable and predetermined offset of the registered images by the increase of the thickness of this layer. In this case the focusing of the acoustic beam can be provided from the surface of the probe and, consequently, good resolution and quality of image can be obtained beginning from the surface of the probe.

FIG. 10a shows the exemplary cross section of the flat transducer with a transparent acoustic spacer. The transducer has piezo electric layer 26 shaped by the grooves of the individual elements with signal electrodes 32, covered by the layer of the isolation substance 33 from the back side of transducer. The front side of the piezo electric layer has the transmit and receive system ground electrodes 30 and 31 connected with the flat impedance matching spacer 20 with a noticeable thickness L (L~5–10 mm). The best termination and, consequently, maximal radiated acoustic power can be obtained for a linear or any other smooth function of the change of the acoustic impedance of the matching spacer along the thickness L. The acoustic impedance of the matching spacer should have the value of the piezo electric material acoustic impedance from the bottom side connected with the transducer and human body impedance from the top side connected with the investigated part of the human body. Such a dependence of the acoustic impedance along the thickness of the spacer can be provided by the use of a composite designed spacer when it is formed from the thin plates of the material with different acoustic impedance.

FIG. 10b, 10c and 10d shows the same views of the acoustic transparent spacers for different kinds of transducers with different shapes of the spacer: acoustic transparent spacer with curved front surface for the flat transducer (FIG. 10b), shape of the spacers for concave transducer with both sides of spacer curved and with a flat top surface (FIG. 10c) and curved spacer for the convex transducer (FIG. 10d).

Figure 11:
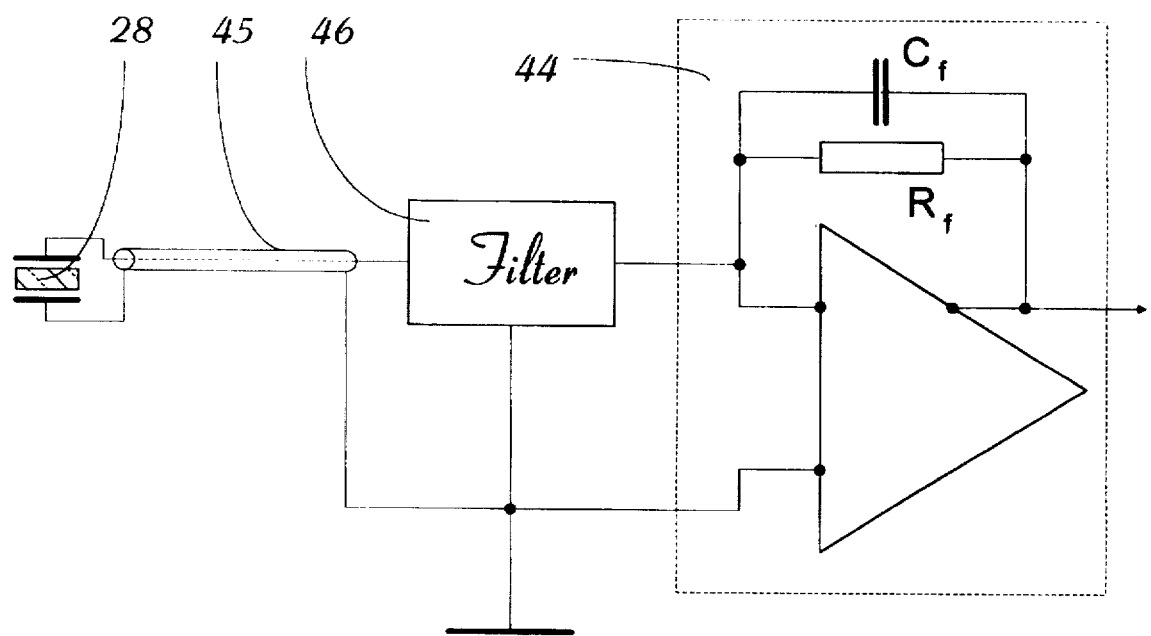
FIG. 11 shows the schematic of the connection of the receive transducer element with amplifier.

The scheme of the receive electronic channel for registration of the echo signals from the investigated object is shown in the FIG. 11. Every individual element 28 of the receive array system is connected with the input of the separate amplifier 44 by a cable 45 and a filter 46. The possibility to separate receive and transmit systems realizes a low noise scheme of amplification for the echo signals. During the reception time every elementary transducer 28 works as a generator of charge and a wide band high impedance amplifier can be used for amplification of the echo signals. It can be radio frequency amplifiers with high impedance inputs, or charge sensitive amplifiers, as it is shown in FIG. 11. Charge sensitive amplifiers are used usually in the same schematics and realize a very low level of noise.

Figure 12:
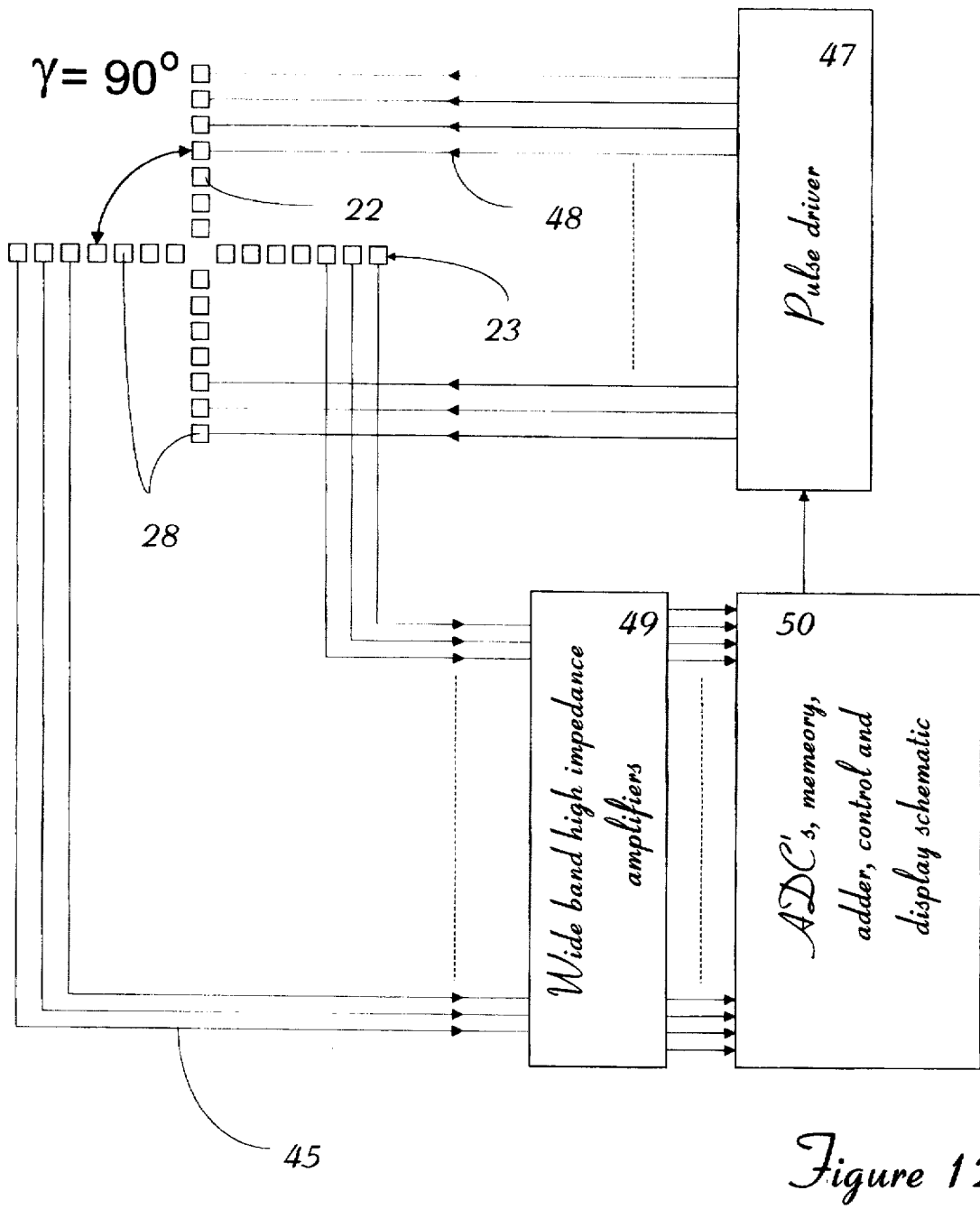
FIG. 12 shows the connection scheme of the transducer with one transmit and one receive array with pulse driver and reception apparatus.

FIG. 12 describes the schematic of the generation of the acoustic wave packages and schematic of the signal processing of the echo signals. As it is seen from the figure, transmit and receive array systems are separated. The pulse driver 47 has timing circuitry and the necessary set of generators. They perform the functions of the transmit system 22 in the phased mode with dynamic focusing and scanning of the beam and are connected with individual elements 28 of the transmit array 22 by cables 48. Individual elements 28 of the receive array 23 register the echo signals and are connected by cables 45 with reception parts 49 and 50 of the apparatus which provides amplification of the echo signals, conversion of them in the digital code and recording of amplitude information from every receive array individual element in the memory for every focal distance. Adjustment of the dynamic receive apertures is produced by shifting the individual element information by the number of digits corresponding to the delay for every individual element. After this, individual element information is summed and presented as part of the acoustic line for every selected aperture. Thus, the sector of the 2D image is formed from information registered during propagation of one acoustic wave package into the investigated media. These parts of the acoustic lines are added to the parts registered from previous focal distances and displayed after completion of the two dimensional image registration. The change of the scan angle for a flat transmit beam allows the registration and display of the next two dimensional image. The three dimensional image can be displayed as a series of two dimensional images.

Another apparatus which reduces the required time for the reconstruction of the two and three dimensional images is comprised of a transducer with single transmit element placed at the center of symmetry of the receive system, an apparatus for amplification, digitization and storage of the digital time and amplitude information, and analysis and display of the reconstructed images.

Figure 13:
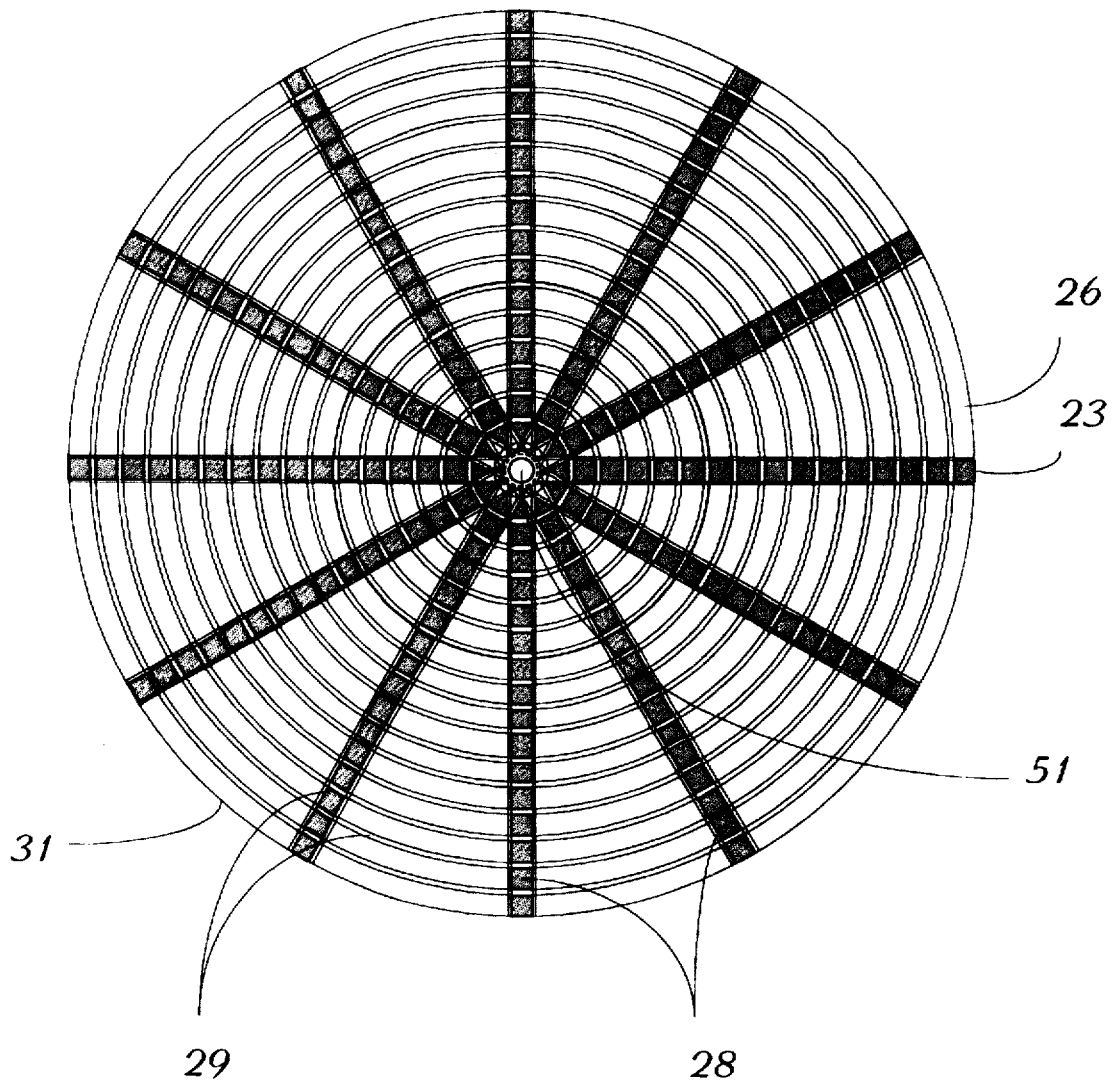
FIG. 13 shows the view of the cross transducer with single transmit element.

An exemplary view of such a transducer is shown in FIG. 13. The transducer is made on a piezo electric disk plate 26. Receive arrays 23 having individual elements 28 produced by cutting the radial and circular grooves 29. Transmit element 51 is placed at the center of the piezo electric material disk 26. The transducer ground electrode 31 is made on the other side of piezo electric material disk 26. The transmit element of the transducer provides the irradiation of a wide unfocused beam into the investigated object. Individual elements of receive arrays provide the reception of the echo signals and are connected with the subsequent apparatus by the cable wiring.

Figure 14:
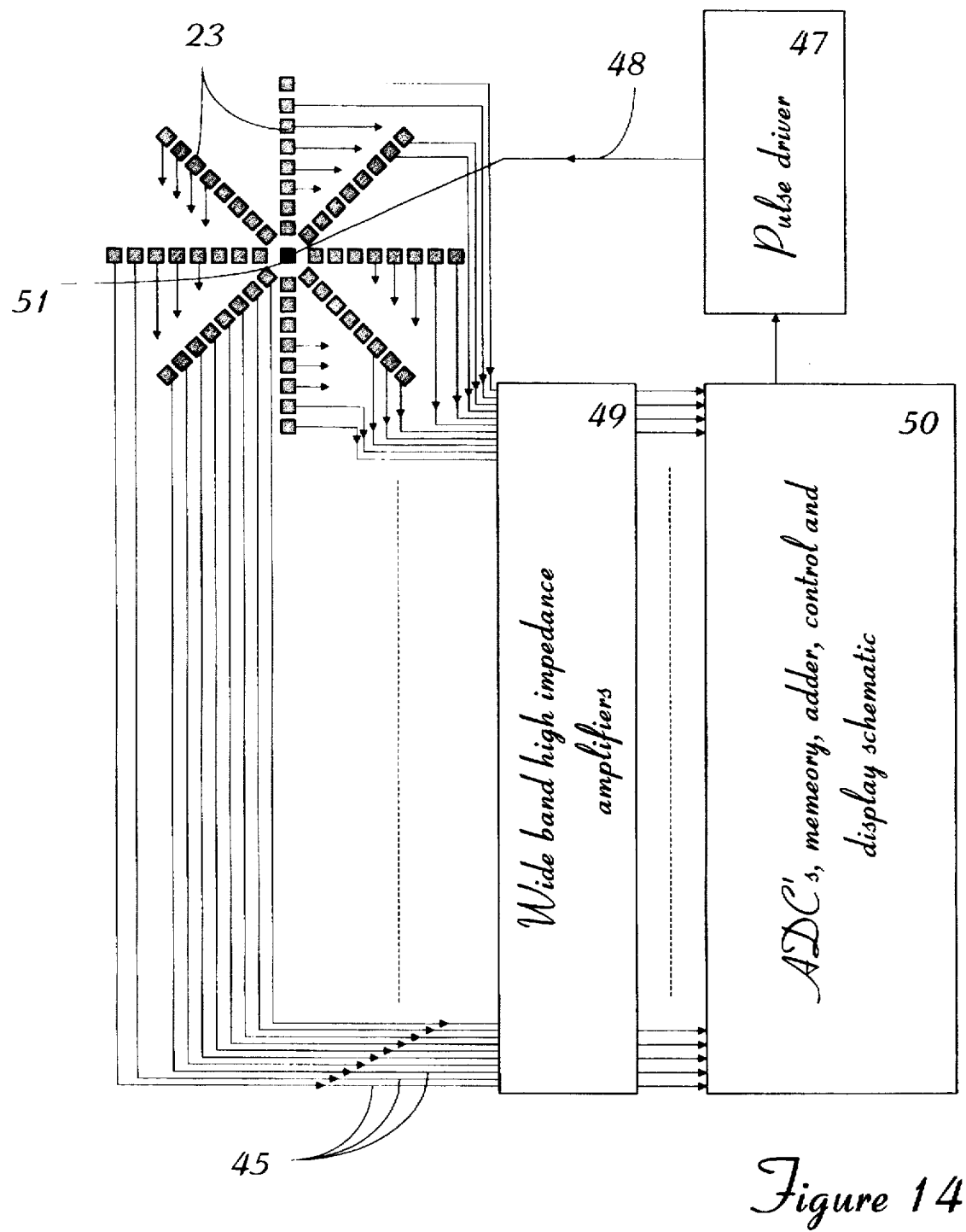
FIG. 14 shows the connection scheme of the single transmit element transducer with the pulse driver and the reception apparatus.

The schematic of an apparatus is shown in FIG. 14. Transmit element 51 of the transducer is driven by the pulse driver 47 through the separate cable 48. The scheme of the pulse driver is very simple in this instance and contains one generator controlled by schematic 50. Individual elements of receive array 23 are connected by the separate cable wiring 45 with the schematics for registration and storage information 49 and 50, respectively. The received echo signals are amplified by wide band high impedance amplifiers 49. The digitization and the storage of the time and amplitude information is produced by schematic 50. This block of the apparatus is comprised of the ADC's for digitization of the received acoustic pulses, memory for storage of the digital information, control schematic and display schematic. Reconstruction of the three dimensional images uses a fast algorithm, which is the same as for the scheme shown in FIG. 12. The fast algorithm includes the synthesis of the scanned and focused receive apertures for receive arrays which is provided by the shifting of the individual element's digital information by a predetermined number of digits and summation of this information for every time point inside the time interval of interest. This time interval is chosen in the vicinity of the selected receive focus. As a result, some part of the acoustic line for the selected focal point is registered. After storage of this part of the acoustic line, the next synthetic aperture with the next focal point is shaped by shifting the individual element's digital information and this cycle of creating part of the acoustic line is repeated. Thus, we obtain a set of acoustic lines placed into the irradiated solid angle and used for creation and display of the two and three dimensional images. As it is shown, one acoustic pulse radiated into the investigated object is enough for registration of a single three dimensional image. Such a fast algorithm allows us to register and reconstruct the Doppler and three dimensional images simultaneously.

We claim:

1. A method of generating a scanned "pencil" acoustic beam comprising the steps of:

shaping one or more dynamic focused and scanned flat transmit acoustic beams by energizing one or more phased transmit arrays, so that said transmit flat acoustic beams can be focused and steered by changing the energizing time of transmit array individual elements, receiving the echo pulses by one or more phased receive arrays with dynamic focused and scanned flat receive apertures, so that said flat receive apertures can be focused and steered by the change in delay of the signals received by individual elements of receive arrays or can be formed by a shift of digitized amplitude information in memory for a predetermined number of digits in accordance with the set flat receive aperture, placing said transmit and receive arrays with axial symmetry and at the same origin, orienting said transmit and receive arrays relative to each other by an optimal angle γ defined as $$\gamma = \pi/(n\ tr + n\ rec)$$

where n tr is the number of said one or more transmit arrays and n rec is the number of said one or more receive arrays, separating the array functions in transmission and reception modes, so that transmit arrays are used only for transmission of acoustic pulses into an investigated part of a human body and receive arrays are used only for reception of echo pulses from an irradiated part of a human body, whereby said scanned "pencil" acoustic beam is generated by a crossing of one or more of said dynamic focused and scanned flat transmit acoustic beams and said one or more dynamic focused and scanned flat receive apertures.

2. An ultrasound cross transducer for three dimensional image reconstruction comprising:

one or more transmit arrays having a plurality of individual elements, every said individual element having a signal electrode from one side of the piezo electric material and ground electrode from the opposite side, said individual elements being connected with a pulse driver and providing only the emission of acoustic wave pulses into the investigated part of a human body, one or more receive arrays having a plurality of individual elements, each said individual element having a signal electrode from one side of the piezo electric material and ground electrode from the opposite side, said individual elements being connected with reception apparatus only, which provides the reception of the echo signals from the individual elements of said arrays, for amplification, digitization and memorization of echo signal amplitudes and displaying of images, said transmit and receive arrays having axial symmetry with the same origin and oriented relative to each other for an optimal angle, said transmit arrays providing the generation of their own flat acoustic beams that can be dynamically focused and scanned by the adjustment in time of the generated acoustic pulses from each transmit array individual element, said receive arrays having flat receive apertures, providing the reception of the echo pulses that can be dynamically focused and scanned by the adjustment in time of echo pulses from each receive array individual element, said transmit arrays being separated from said receive arrays and having one or more ground electrodes joined by an external mounting and forming a transmit ground electrode, said receive arrays being separated from said transmit arrays and having a plurality of ground electrodes joined by an external mounting and forming a receive ground electrode, said transmit and receive array ground electrodes being joined with a common ground electrode of the apparatus at one point.

3. An ultrasound cross transducer as recited in claim 2 and having one said transmit array placed on a rectangular plate of piezo electric material and one said receive array placed on two plates of piezo electric material and joined with the transmit array plate at the center, said transmit array being separated from said receive array and having a separate ground electrode, said receive array big oriented relative to said transmit array by an optimal angle and separated from said transmit array and having two separate ground electrodes joined by said external mounting.

4. An ultrasound cross transducer as recited in claim 3 and having said individual elements of arrays formed by grooves parallel to the sides of said transmit and receive piezo electric material plates and ground electrodes placed on another side of the piezo electric material plates, said ground electrodes being separated and isolated from each other by grooves that are cut along the sides of the piezo electric material plates forming said receive array, one of said ground electrodes being placed on the opposite side of the piezo electric material plate with said transmit array and forming the transmit ground electrode, two others being placed on the opposite side of said piezo electric material plates with said receive array and joined by the external mounting and forming the receive ground electrode.

5. An ultrasound cross transducer as recited in claim 3 and having a receive array without a central individual element.

6. An ultrasound cross transducer as recited in claim 2 and having transmit and receive arrays placed on the same squared piezo electric material plate along diagonals of the plate, said transmit and receive arrays being separated from each other and have separated ground electrodes joined by the external mounting into separate transmit and receive ground electrodes.

7. An ultrasound cross transducer as recited in claim 6 and having individual elements of arrays formed by grooves manufactured in parallel to the diagonals of the squared piezo electric material plate.

8. An ultrasound cross transducer as recited in claim 6 and having grooves cut on the ground electrode side which provide the isolation between transmit and receive ground electrodes.

9. An ultrasound cross transducer as recited in claim 6 and having said transmit and receive arrays without central individual elements.

10. An ultrasound cross transducer as recited in claim 2 and having two transmit and two receive arrays of said arrays manufactured on sectors of a piezo electric material.

11. An ultrasound cross transducer as recited in claim 10 and having individual elements of arrays formed by grooves cut on one side of piezo electric material sectors which provide the isolation between the individual element signal electrodes, having a plurality of transmit and receive ground electrodes separated by grooves manufactured on opposite sides of piezo electric material sectors, joined by the external mounting which form separate transmit and receive ground electrodes.

12. An ultrasound cross transducer as recited in claim 2 and having said plurality of transmit and receive arrays manufactured on the same squared piezo electric material plate, with said transmit arrays along a central column and row of said squared piezo electric material plate, and with said receive arrays along both diagonals of said squared piezo electric material plate.

13. An ultrasound cross transducer as recited in claim 12 and having individual elements of said arrays formed by grooves parallel to the columns and rows on one side of said square piezo electric material plate, and a plurality of transmit and receive ground electrodes separated by grooves along both sides of said transmit arrays placed along the central column and row of said square piezo electric material plate, with said grooves providing the isolation of the transmit and receive ground electrodes.

14. An ultrasound cross transducer as recited in claim 12 and having a plurality of said transmit and receive arrays without central individual elements.

15. An ultrasound cross transducer as recited in claim 2 and having three transmit arrays and three receive arrays of said arrays manufactured on a piezo electric material disk.

16. An ultrasound cross transducer as recited in claim 15 and having individual elements of said arrays formed by circular and radial grooves on one side of said piezo electric material disk and a plurality of transmit and receive ground electrodes on an opposite side separated by the radial grooves and joined to separate transmit and receive ground electrodes by the external mounting.

17. An ultrasound cross transducer as recited in claim 2 and having a plurality of said transmit and receive arrays manufactured upon a composite material wafer and having increased area of said individual element signal electrodes.

18. An ultrasound cross transducer as recited in claim 2 and having concave shaped transmit and receive arrays of said arrays with a plurality of ground electrodes, joined by the mounting which forms the separate transmit and receive ground electrodes.

19. An ultrasound cross transducer as recited in claim 2 and having convex shaped transmit and receive arrays of said arrays with a plurality of ground electrodes, joined by the mounting which forms the separate transmit and receive ground electrodes.

20. An ultrasound cross transducer as recited in claim 2 and having an impedance matching layer with increased thickness, said impedance matching layer providing the dynamic focusing of the acoustic beam beginning from the surface of the transducer.

21. An ultrasound cross transducer as recited in claim 2 and wherein every said receive array has a plurality of the individual element signal electrodes, each said individual element being connected through a separate cable and filter with its own charge sensitive amplifier.

22. A method of reconstruction of three dimensional acoustic images comprising the steps of:

shaping a dynamically focused and scanned flat transmit acoustic beam by the energizing of a separate phased transmit array, so that said flat transmit acoustic beam can be focused and scanned by changing the time of the transmit array individual element energizing, receiving the echo pulses by one or more phased receive arrays with flat receive apertures, placing said transmit array and said receive arrays with axial symmetry and the same origin, orienting said transmit array and said receive arrays relative to each other by an optimal angle γ, said optimal angle γ being given by $$\gamma = \pi/(1+n \text{ rec})$$

where n rec is the number of said receive arrays, energizing said transmit array individual elements and an irradiation of a sector of an investigated part of a human body by said flat transmit acoustic beam with a set focal distance and scan angle, amplifying the acoustic echo pulses received by receive array individual elements, digitizing received amplitude and time information and storing said digitized amplitude and time information in memory, acquiring an acoustic line part by a synthesis of a flat receive aperture with a set focal point so that a shift of digitized amplitude information from said receive array individual elements by a predetermined number of digits in accordance with said flat receive aperture is made, summing said digitized amplitude information for every time near said set focal point and storing said acoustic line part in memory, acquiring other acoustic line parts by a synthesis of flat receive apertures with other focal points into said irradiated sector of an investigated part of a human body, storing said acoustic line parts in memory and shaping a part of a two dimensional acoustic image for a set transmit focal distance, irradiating said sector of an investigated part of a human body by said flat transmit acoustic beam with other focal distances, shaping said parts of a two dimensional acoustic image for other focal distances and forming a two dimensional acoustic image in the memory by joining said parts of two dimensional acoustic images for different focal distances, irradiating other sectors of an investigated part of a human body shifted relatively to each other by a set of other scan angles of a flat transmit acoustic beam, acquiring and storing in the memory of two dimensional acoustic images for said other sectors of an investigated part of a human body, different focal distances and other scan angles, whereby said reconstruction of three dimensional acoustic images is provided by said irradiation of sectors of an investigated part of a human body by flat transmit acoustic beam, said acquisition of two dimensional acoustic images of radiated sectors of an investigated part of a human body and displaying of said two dimensional acoustic images as a time series.

23. An ultrasound apparatus for reconstruction of three dimensional images comprising:

an ultrasound cross transducer with a transmit array having a plurality of individual elements, every said individual element having a signal electrode on one side of a piezo electric material and a ground electrode on the opposite side, said individual elements being connected with a pulse driver and providing only the emission of acoustic wave packages into a sector of an investigated part of a human body, an ultrasound cross transducer comprising one or more receive arrays having a plurality of individual elements, each said individual element having a signal electrode on one side of a piezo electric material and a ground electrode on the opposite side, said individual elements being connected with reception apparatus only and providing the reception of the echo signals from an irradiated sector of an investigated part of a human body, said ultrasound cross transducer having said transmit array and receive arrays placed with axial symmetry and a common origin and oriented relative to each other for an optimal angle, said transmit array providing the generation of a flat acoustic beam into a sector of an investigated part of a human body, said flat acoustic beam capable of being dynamically focused and scanned for irradiation of different sectors of an investigated part of a human body by the adjustment in time of the generated acoustic pulses from each transmit array individual element, said receive arrays having flat receive apertures providing the reception of the echo pulses from said sectors of an investigated part of a human body, said transmit array being separated from said receive arrays and having its own ground electrode, said receive arrays being separated from said transmit array and have a plurality of ground electrodes joined by the external mounting which forms a receive ground electrode, said transmit and receive ground electrodes being joined with a common ground electrode of the apparatus at one point, a pulse driver which provides the energizing of said transmit array individual elements with a predetermined time sequence for shaping the flat acoustic beam for an irradiation of sectors of an investigated part of a human body with different focal distances and scan angles, an apparatus having amplifiers, fast analog digital converters and memory for recording time and amplitude digital information from each said receive array individual element, an apparatus having adder, memory, control and display elements for providing an acquisition of two dimensional acoustic images of different sectors of an investigated part of a human body irradiated by said transmit array and display of said two dimensional acoustic images, whereby said reconstruction of three dimensional images is provided by an ability of said flat acoustic beam to irradiate different sectors of an investigated part of a human body with different scan angles, by a capability of said apparatus to reconstruct two dimensional acoustic images of said different sectors of an investigated part of a human body and display them as a time series.

24. An ultrasound apparatus for reconstruction of the three dimensional images comprising:

an ultrasound cross transducer having a sole transmit element with a signal electrode from one side of a piezo electric material and a ground electrode from the opposite side, said individual element being connected with a pulse driver and providing only the emission of an unfocused acoustic beam into a solid angle of an investigated part of a human body, an ultrasound cross transducer having more than one receive arrays having a plurality of individual elements, each said individual element having a signal electrode from one side of a piezo electric material and a ground electrode from the opposite side, said individual elements being connected with reception apparatus only and providing the reception of the echo signals from an irradiated solid angle of an investigated part of a human body, said receive arrays having flat receive apertures and placed with axial symmetry and a common origin and oriented relative to each other for some angle, a pulse driver which provides the energizing of said sole transmit element, an apparatus having amplifiers, fast analog digital converters and memory for recording time and amplitude digital information from each receive array individual element, an apparatus having adder, memory, control and display elements for providing an acquisition of two dimensional acoustic images into said solid angle of an investigated part of a human body irradiated by said sole transmit element and display of said two dimensional acoustic images, whereby said reconstruction of three dimensional images is provided by an ability of said unfocused acoustic beam to irradiate a solid angle of an investigated part of a human body, by a capability of said apparatus to reconstruct the two dimensional acoustic images into said solid angle of an investigated part of a human body and to display them as a time series.

* * * * *

UNITED STATES PATENT AND TRADEMARK OFFICE
CERTIFICATE OF CORRECTION

PATENT NO. : 5,797,845
DATED : August 25, 1998
INVENTOR(S) : Leonid S. Barabash, et. al.

It is certified that error appears in the above-identified patent and that said Letters Patent is hereby corrected as shown below:

In column 2, lines 61 change

" $n_{rac}$ " to -- $n_{rec}$ --

In column 2, lines 60 - 63 change

"$n_{tr}$ is the number of transmit array individual elements and $n_{rac}$ is number of receive array individual elements." to -- $n_{tr}$ is the number of transmit arrays and $n_{rec}$ is the number of receive arrays. --

In column 12 (Claim 1), line 25 change

" $\gamma = \pi \, ( n\, tr + n\, rec )$ " to

-- $\gamma = \pi / ( n\, tr + n\, rec )$. --

Signed and Sealed this

Seventh Day of March, 2000

Attest:

Q. TODD DICKINSON

Attesting Officer

Commissioner of Patents and Trademarks